United States Patent [19]

Prout et al.

[11] Patent Number: 5,049,677

[45] Date of Patent: Sep. 17, 1991

[54] BISMUTH SALT STABILIZERS FOR 3-ISOTHIAZOLONES

[75] Inventors: James G. Prout, Erdenheim; Andrew B. Law, Newtown; Gary L. Willingham, Glenside, all of Pa.

[73] Assignee: Rohm and Haas Company, Philadelphia, Pa.

[21] Appl. No.: 356,979

[22] Filed: May 24, 1989

[51] Int. Cl.$^5$ .................... A01N 25/34; C07D 275/02
[52] U.S. Cl. ..................... 548/213; 252/175; 424/404; 424/409; 424/414
[58] Field of Search ............... 548/103, 213; 252/175; 424/404, 409, 414

[56] References Cited

U.S. PATENT DOCUMENTS

| | | | |
|---|---|---|---|
| 3,523,121 | 8/1970 | Lewis et al. | 548/513 |
| 3,761,488 | 9/1973 | Lewis et al. | 548/513 |
| 3,870,795 | 3/1975 | Miller et al. | 548/513 |
| 4,067,878 | 1/1978 | Miller et al. | 548/513 |
| 4,129,448 | 12/1978 | Greenfield et al. | |
| 4,150,026 | 4/1979 | Miller et al. | 548/513 |
| 4,165,318 | 8/1979 | Greenfield et al. | |
| 4,241,214 | 12/1980 | Miller et al. | 548/513 |
| 4,783,221 | 11/1988 | Grove | |
| 4,804,616 | 2/1989 | Ueda et al. | 430/379 |
| 4,830,948 | 5/1989 | Ishikawa et al. | 430/372 |

FOREIGN PATENT DOCUMENTS 44-42915  6/1969  Japan.

OTHER PUBLICATIONS

Kathon 886 MW Microbiocide and Kathon 893 MW Fungicide: Analysis in Metalworking Fluids by High-Performance Liquid Chromatography, Rohm and Haas, 1988.

*Primary Examiner*—C. Warren Ivy
*Assistant Examiner*—Celia Chang
*Attorney, Agent, or Firm*—Michael B. Fein

[57] ABSTRACT

Bismuth salt stabilizers are used to stabilize various isothiazolones which are normally neat or in solution. These compositions exhibit bactericidal, fungicidal and algaecidal properties.

21 Claims, No Drawings

BISMUTH SALT STABILIZERS FOR 3-ISOTHIAZOLONES

BACKGROUND OF THE INVENTION

1. Field of the Invention

This invention relates to stable compositions of 3-isothiazolones, their preparation, and their use in controlling living organisms.

2. Description of the Prior Art

Isothiazolones have generated high commercial interest as stabilizers against spoilage caused by microorganisms of a large number of aqueous and non-aqueous products subject to such spoilage. Isothiazolones are highly effective and, by suitable choice of the functional groups, broadly useful. However, it was early recognized that either in storage prior to addition to the matrix to be stabilized or after addition, their efficacy was decreased because the isothiazolone was not stable under practical conditions of long-term storage. Means have thus been sought from the beginning of research with such compounds to improve their stability.

U.S. Pat. Nos. 3,870,795 and 4,067,878 teach the stabilization of isothiazolones against chemical decomposition by addition of a metal nitrite or metal nitrate, but teach that other common metal salts, including carbonates, sulfates, chlorates, perchlorates, and chlorides are ineffective in stabilizing solutions of isothiazolones, such solutions usually being in water or in an hydroxylic solvent. Bismuth is not taught or considered in these patents.

U.S. Pat. Nos. 4,150,026 and 4,241,214 teach metal salt complexes of isothiazolones useful because of their enhanced thermal stability, while retaining biological activity. The metal salts listed do not include bismuth.

Japanese Kokai 72-014476 teaches bismuth salts, among other metal salts, of benzisothiazolones useful as bactericidal agents. Such salts would be limited to the structure of the benzisothiazolone where N is substituted with H. Further, the isothiazolones which are not fused to a benzene ring are not considered.

It is known to use certain organic stabilizers for isothiazolones, generally for use situations where metal salts may create problems, such as corrosion, coagulation of latices, insolubility in non-aqueous media, interaction with the substrate to be stabilized, and the like. Formaldehyde or formaldehyde-releasing chemicals are known as stabilizers, (see U.S. Pat. Nos. 4,165,318 and 4,129,448), as are certain organic chemicals such as orthoesters (U.S. application Ser. No. 118,366) and epoxides (U.S. application Ser. No. 194,234).

Grove, U.S. Pat. No. 4,783,221 teaches blends of the isothiazolones of the present invention with at least one metal salt of an organic carboxylic acid of at least six carbon atoms, wherein the metal is a transition metal, zinc, mercury, antimony, or lead, and also with a solvent diluent. The patent is directed to wood preservative compositions and does not teach or suggest use in emulsion stabilization, or paint films applied from said latices, or in metalworking fluids. Further, Grove does not teach or exemplify bismuth.

In certain applications, however, it is desirable to avoid addition of organic stabilizers by virtue of their volatility, decomposition under high heat, higher cost, difficulty in handling, potential toxicity, and the like. Formaldehyde is a suspected carcinogen, and it is desirable not to use formaldehyde in applications where contact with human skin or lungs may occur.

In actual use, copper salts, such as copper sulfate, have proved efficacious in stabilization of isothiazolones. However, copper salts may be undesirable in effluent streams in such operations as in the manufacture of stabilized isothiazolones or in their blending into a product or the use of that product. Copper salts, especially the chlorides, may contribute to possible corrosion, or in the presence of polymers in aqueous dispersion may lead to coagulation of the dispersion.

SUMMARY OF THE INVENTION

It has become an object of the invention to provide a stabilization system for isothiazolones which overcomes some or all of the disadvantages of prior art systems. It is also an object to provide a stabilized isothiazolone which uses low levels of stabilizer so as to avoid interference with other components in systems in which isothiazolones are used as microbiocides.

These objects, and others which will become apparent from the following disclosure, are achieved by the present invention which comprises in one aspect a stabilized composition comprising:

a) a compound of the formula

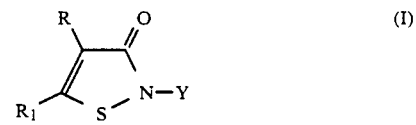

where Y is substituted or unsubstituted alkyl, unsubstituted or halo substituted alkenyl or alkynl, unsubstituted or substituted cycloalkyl, aralkyl, aryl, or hydrogen, and R and $R_1$ are hydrogen, halo or alkyl;

b) a stabilizing amount of a bismuth salt.

In another aspect, the invention comprises a method for inhibiting the growth of bacteria, fungi, yeast or algae in a locus subject to contamination by bacteria, fungi, yeast or algae, which comprises incorporating onto or into the locus, in an amount which is effective to adversely affect the growth of bacteria, fungi, yeast, or algae, the aforementioned composition.

DETAILED DESCRIPTION OF THE INVENTION AND THE PREFERRED EMBODIMENTS

The isothiazolones which are stabilized include those disclosed in U.S. Pat. Nos. 3,523,121 and 3,761,488 as represented by the following structural formula:

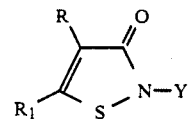

wherein Y is an unsubstituted or substituted alkyl of from 1 to 18 carbon atoms, an unsubstituted or halo substituted alkenyl or alkynyl of from 2 to 8 carbon atoms, preferably, from 2 to 4 carbon atoms, an unsubstituted or substituted cycloalkyl of from 5 to 8 carbon atoms, an unsubstituted or substituted aralkyl, an unsubstituted or substituted aryl, or hydrogen; R is hydrogen, halo, or a (C1-C4)alkyl and $R_1$ is hydrogen, halo or (C1-C4)alkyl.

Representative Y substituents include methyl, ethyl, propyl, isopropyl, butyl, hexyl, octyl, cyclohexyl, benzyl, 3,4-dichlorobenzyl, 4-methoxybenzyl, 4-chlorobenzyl, 3,4-dichlorophenyl, 4-methoxyphenyl, hydroxymethyl, chloromethyl, chloropropyl, hydrogen, and the like.

Preferred isothiazolones are 5-chloro-2-methyl-3-isothiazolone, 2-methyl-3-isothiazolone, 2-n-octyl-3-isothiazolone, 4,5-dichloro-2-cyclohexyl-3-isothiazolone and 4,5-dichloro-2-octyl-3-isothiazolone.

Especially preferred is 5-chloro-2-methyl-3-isothiazolone, either as a sole compound or in admixture with 2-methyl-3-isothiazolone. When in admixture, the preferred ratio of monochlorinated/unchlorinated isothiazolone is from about 70:30 to about 85:15, and an especially preferred ratio is from about 70:30 to about 80:20. A second especially preferred isothiazolone is 2-methyl-3-isothiazolone in combination with low levels of 5-chloro-2-methyl-3-isothiazolone, a preferred ratio being from about 98:2 to about 96:4, and an especially preferred ratio being about 97:3.

This invention comprises a composition which contains from about 0.0001 to about 99.999 parts of one or more isothiazolones and a stabilizing amount of a bismuth salt, in the range of from about 0.0001 to about 99.9 parts.

More preferably, the composition comprises at least one isothiazolone wherein Y is $(C_1-C_{18})$alkyl or $(C_3-C_{12})$cycloalkyl; R is hydrogen, methyl, or chloro; and $R_1$ is hydrogen or chloro. Typical formulation ranges are illustrated in the following Table (all percentages are parts by weight) for both a concentrated solution of the isothiazolone and a dilute solution. For certain uses, such as shipping of large quantities, more concentrated solutions may also be utilized.

FORMULATIONS TABLE

| Isothiazolone | Bismuth Salt | Solvent |
| --- | --- | --- |
| (I, Supra) 0.0001-99.9999% | 0.0001-99.9% | 0-99.9998% |
| Preferred (dilute) 0.001-50% | 0.0001-10% | 40-99.9998% |
| Preferred (conc) 1-25% | 0.1-10% | 65-98.9% |

A wide variety of bismuth salts are known to the art. These include the halides, oxyhalides, sulfides, basic sulfate, basic nitrate, borate, camphorsulfonate, perchlorate, basic perchlorate, orthophosphate, basic dichromate, and the like. Also known are salts with organic acids, such as the citrate, oxalate, octoate, tartrate, partial tartrate, salicylate, basic salicylate, 2-ethylhexanoate, neodecanoate, undecylenate, naphthenate, oleate, benzoate, lactate, propionate, partial propionate, acetate, basic acetate, and the like. Preferred for the present use are the salts of organic acids. Especially preferred for use in aqueous systems are the water-soluble salts of organic acids. Unless otherwise specified, parts of a bismuth salt refers to the parts of bismuth (+3) present.

Solvents may be used to dissolve the isothiazolones and may be any organic solvent which dissolves the isothiazolones, is compatible with the proposed end use, does not destabilize the isothiazolone, and does not react with the bismuth salt to eliminate its stabilizing action.

Hydroxylic solvents, for example, polyols, such as glycols, alcohols and the like, may be used. Under conditions of high dilution and high ratios of stabilizer to isothiazolone, glycols may be successfully used. In certain formulations, hydrocarbons, either aliphatic or aromatic, are useful solvents.

Preferred solvents are capped polyols, wherein the free hydroxyl group is replaced with an ether or ester function. Especially preferred are 2,5,8,11-tetraoxadodecane, commonly known as triethylene glycol dimethyl ether, and 4,7-dioxaundecanol-1 acetate, commonly known as diethylene glycol butyl ether acetate.

Water is a solvent for certain of the preferred isothiazolones and the bismuth salts may be employed in aqueous formulations.

The amounts of bismuth salt employed will vary depending on use conditions and concentrations of the isothiazolone in the mixture. In more concentrated solutions, effective amounts of bismuth salt based on isothiazolone are in the ratios of from about 1:50 to about 2:1. Obviously higher amounts may be used, but at additional cost. At high levels of dilution of the isothiazolone (such as from 1 to 10,000 ppm isothiazolone in the solvent), the ratio of stabilizer to isothiazolone can range from about 1:10 to about 10:1.

The stabilization advantages of the bismuth salts are noted even when the isothiazolone contains other salt stabilizers recorded in U.S. Pat. Nos. 3,870,795, 4,067,878, 4,150,026 and 4,241,214.

Uses of these new organically stabilized biocides are typically at any locus subject to contamination by bacteria, fungi, yeast or algae. Typically loci are in aqueous systems such as water cooling, laundry wash water, oil systems such as cutting oils, oil fields and the like where microorganisms need to be killed or where their growth needs to be controlled.

Because isothiazolone biocides are so active, the low level of bismuth salts required to achieve stabilization also makes them ideal when compared to many known biocides because at the low levels required they are not likely to interfere with other components in systems requiring protection or with systems upon which the protected systems will be applied.

Potential areas of general application include deodorizers, liquid and powder soaps, skin removers, oil and grease removers, food processing chemicals, dairy chemicals, food preservatives, animal food preservatives, wood preservation, paint, lazures, stains, mildewcides, hospital and medical antiseptics, metal working fluids, cooling water, air washers, petroleum production, paper treatment, petroleum products, adhesives, pigment slurries, latexes, leather and hide treatment, agricultural formulations, mining, nonwoven fabrics, petroleum storage, rubber, sugar processing, tobacco, cosmetics, chemical toilets, household laundry products, diesel fuel additives, waxes and polishes and many other applications where water and organic materials come in contact under conditions which allow the growth of undesired microorganisms.

Isothiazolones also are used as biocides, in oil field water treatment, as watercooling system microbicides, as preservatives for aqueous dispersions or organic polymers, as wood pulp white water slimicides, as cosmetic preservatives, as cutting oil, jet fuel, and heating oil preservatives, and the like. They are also useful in adhesives, agricultural chemical preservation, air washing devices, alcohol stabilization, carpet backing, caulks and sealants, ceramics, cleaners, cement modifiers, diesel and other fuels, electrocoating systems, electronic circuitry, commercial enzymes, fabric softeners, feed preservation, fibers, printing, household and industrial cleaners, inks, laundered goods, laundry wash water, marine antifoulants, such as fishnets, propellors, ship bottoms, and the like, medical devices, membranes, odor control, pasteurization baths, photographic emulsions, pharmaceutical and therapeutic uses, preservation of reagent chemicals, sanitizers, swimming pools, textile manufacture and uses, toiletries, waste treatment, water purification, and the like.

Solutions of isothiazolones are also applied to a solid substrate, such as fabric, leather, or wood, as a preservative, or admixed with plastics.

Metal working fluids are proprietary combinations of chemicals, which may contain such ingredients as are listed, but are not limited to such: alkanolamines, petroleum sulfonate surfactants, oils (naphthenic, paraffinic, etc.), chlorinated paraffins and fatty esters, sulfurized fatty compounds, phosphate esters, fatty acids and their amine salts, glycols, polyglycols, boric acid esters and amides. They are utilized in the milling, machining, drilling, and other processing technologies for fabricating metal for the purposes of lubricating, cooling, preventing surface corrosion, and the like. They are sold at various levels of active MWF concentrate, and are diluted in use to 1-10% ingredients in water.

Because metal working fluids are recycled and stored, the growth of microorganisms is favored. Isothiazolones have been found effective in preventing the growth of such organisms. Certain of the components in the metal working fluids will tend to destroy the isothiazolone and so remove its biocidal protective activity, so that stabilizers for the isothiazolone against such degradation are desirable.

It is known in the art that the performance of biocides can frequently be enhanced by combination with one or more other biocides. In fact, there have been numerous examples of synergistic combinations of biocides. Thus, other known biocides may be combined advantageously with the stabilized isothiazolones of this invention.

The examples are intended to illustrate the present invention and not to limit it except as it is limited by the claims. All percentages are by weight unless otherwise specified, all temperatures in degrees Centigrade, and all reagents are of good commercial quality unless otherwise specified. Methods for quantitative determination of the isothiazolones in the following examples in metal-working fluids are described in detail in "Kathon 886 MW Microbicide and Kathon 893 MW Fungicide: Analysis in Metalworking Fluids by High-Performance Liquid Chromatography", 1988, Rohm and Haas Company.

EXAMPLES

Examples 1 to 3

These examples demonstrate the stabilizing effect of bismuth salts for isothiazolones added to several different metal working fluids (MWF). MWF concentrates A and B were "semi-synthetic" types having about 10 to 15 percent naphthenic/paraffinic oil, about 50 percent water, emulsifying agents, pH adjusting amines, anticorrosive agents, and EP (extreme pressure) agents. MWF concentrates C through E were synthetic types having about 70 percent water, 15 percent long chain nonionic surfactants or esters, 15 percent phosphate or amine carboxylate corrosion inhibitor, pH adjusting amines, and EP agents.

Into a glass vial in the following order were placed: a) 5 parts by weight of the MWF concentrate, b) 5 parts of the stabilizer in solution or dispersion, c) 5 parts water, d) 5 parts of an aqueous solution containing 80 ppm active ingredient (AI), prepared by dilution of a 14.4% aqueous solution of an approximately 75/25 mixture of 5-chloro-2-methyl-3-isothiazolone and 2-methyl-3-isothiazolone, the former being considered the active ingredient for these purposes; also present was 9.2 weight percent magnesium chloride and 15.7% magnesium nitrate.

Thus the final mixture contained 3-5% of the MWF concentrate, 15 ppm active ingredient of the isothiazolone, and 0 (control) to 40 ppm of the bismuth stabilizer.

The vials were then capped, stored at ambient room temperature in a closed cabinet for a designated time, filtered through a 0.45 micron filter into another vial and analyzed the same day. The relative concentration of the active ingredient was determined by reverse phase high pressure liquid chromatography, utilizing a Varian model 5500 chromatograph and an ultraviolet detector.

TABLE 1

STABILIZATION OF 5-CHLORO-2-METHYL-3-ISOTHIAZOLONE IN MWF CONCENTRATE A WITH BISMUTH SALTS AFTER THREE DAYS

| Stabilizer | ppm $Bi^{+3}$ | % AI remaining |
|---|---|---|
| None | — | 20 |
| Bismuth sodium tartrate | 1.3 | 42 |
| " | 2.5 | 52 |
| " | 5 | 63 |
| " | 10 | 69 |
| " | 20 | 69 |
| " | 40 | 71 |
| Bismuth octoate | 1.3 | 38 |
| " | 2.5 | 48 |
| " | 5 | 58 |
| " | 10 | 63 |
| " | 20 | 70 |
| " | 40 | 80 |

Note: original system contained 15 ppm 5-chloro-2-methyl-3-isothiazolone (AI) with 3% MWF Concentrate A

Example 2

This example demonstrates the stabilizing effect of bismuth sodium tartrate on a variety of commercial MWFs after 11 days at room temperature. Testing was as in Example 1. In the absence of the MWF, the relative concentration of the AI remained at 100%.

TABLE 2

METAL WORKING FLUIDS STABILIZED WITH BISMUTH AGED 11 DAYS

| Working Fluid, conc., % | | Stabilizer, ppm | | AI, % remaining |
|---|---|---|---|---|
| MWF Concentrate A | 3.3 | — | | 0 |
| " | " | Bi | 5 | 20 |
| " | " | " | 10 | 25 |
| " | " | " | 20 | 30 |
| MWF Concentrate D | 4.0 | — | | 46 |
| " | " | Bi | 5 | 71 |
| " | " | " | 10 | 78 |
| " | " | " | 20 | 76 |
| MWF Concentrate B | 5.0 | — | | 56 |
| " | " | Bi | 5 | 79 |
| " | " | " | 10 | 81 |
| " | " | " | 20 | 84 |
| MWF Concentrate C | 5.0 | — | | 55 |
| " | " | Bi | 5 | 93 |
| " | " | " | 10 | 93 |
| " | " | " | 20 | 88 |

Example 3

In this experiment, further results are shown for a variety of bismuth salts in two different MWFs. The bismuth salts tested were readily soluble in the test system; there was no color development with the bismuth systems on mixing.

TABLE 3
COMPARISON OF SEVERAL BISMUTH SALTS IN TWO MWF SYSTEMS AFTER 11 DAYS

| Stabilizer | Bi/ ppm | MWF Conc. E % AI Remaining | MWF Conc. A % AI Remaining |
|---|---|---|---|
| None | — | 0 | 0 |
| Bi citrate | 20 | 68 | 32 |
| BiNa tartrate | 20 | 68 | 33 |
| BiK tartrate | 20 | 69 | 32 |
| Bi tartrate | 20 | 69 | 31 |
| Bi oxalate | 20 | 68 | 28 |
| Bi phosphate | 20 | 69 | 22 |
| Bi sulfate | 20 | 70 | 22 |
| Bi lactate | 20 | 69 | 32 |
| Bi ammonium citrate | 20 | 70 | 32 |

Example 4

This example illustrates the ability of bismuth salts to stabilize the isothiazolone in the absence of any other metal salts. A mixture of 5-chloro-2-methyl-3-isothiazolone and 2-methyl-3-isothiazolone (75/25 ratio) was isolated without alkaline- earth hydroxide neutralization; thus no salts were present prior to preparation of the test mixture. This "free base" at 1.5 parts AI in 100 parts water was stored for 7 days at 40° C. and analyzed as in the previous examples. The AI was totally decomposed under these conditions. When 1 part of bismuth, added as the octoate, the sodium tartrate, or the potassium tartrate, was also present, the AI content after 7 days was approximately 50% for all three salts.

Examples 5-6

These examples illustrate the ability of bismuth salts to be used in stabilization of isothiazolones used as mildewcides in paint formulations. The water-based paint formulation was prepared from standard ingredients, utilizing a commercial acrylic-based latex with conventional pigments, dispersants, and the like.

To two sealable containers were charged 100 parts of the paint formulation. To one was charged twice the desired final stabilizer concentration, and to the other, twice the desired isothiazolone concentration. Both portions were homogenized for 15 minutes each, then blended and re-mixed. The sealed containers were stored at 60° C. Samples were removed at 0, 5 and 10 days.

To 1 part of the sample was added 9 parts propylene glycol, the diluted sample shaken for one hour, centrifuged at 70,000 rpm for 30 minutes, the supernatant diluted with two volumes of methanol, and that solution filtered through a 0.45 micron filter. The filtered sample was injected directly into the HPLC described in Example 1. Appropriate analytical calibrations were made for the various isothiazolones studied.

The bismuth octoate was added from a mineral oil dispersion and the bismuth sodium tartrate from an aqueous dispersion in amounts to give the dilutions indicated. The mixture of 2-methyl-3-isothiazolones was from a 14.4% AI aqueous dispersion, which also contained the concentrations of magnesium chloride and magnesium nitrate as noted in Example 1. The 2-octyl-3-isothiazolone was added as a 45.5 wt. % solution in propylene glycol. The 4,5-dichloro-2-octyl-3-isothiazolone was added as a 34% solution in xylene. No other salt was present in either of the octyl compounds when added to form the test mixture. The following formulation is a typical paint blend for testing of stabilization against microbial activity. Texanol (R) is trimethyl-1,3-pentanediol monoisobutyrate supplied by Eastman Chemical. "Latex" is a latex of a copolymer of butyl acrylate and methyl methacrylate.

TABLE 4
LATEX PAINT FORMULATION

| Material | lb/50 gal | g/l |
|---|---|---|
| Natrosol 250 MHR hydroxyethyl cellulose | 1.5 | 3.6 |
| Ethylene glycol | 12.5 | 30 |
| Premix | | |
| Water | 56.0 | 134.4 |
| Tamol 960 (40%) poly(methacrylic acid) | 3.6 | 8.6 |
| Potassium tripolyphosphate | 0.75 | 1.8 |
| Triton CF-10 surfactant | 1.3 | 3.1 |
| Colloid 643 thickener | 0.5 | 1.2 |
| Propylene glycol | 17.0 | 40.8 |
| Ti-Pure R-902 titanium dioxide | 112.5 | 270 |
| Minex 4 filler pigment | 79.7 | 191.3 |
| Icecap K filler pigment | 25.0 | 60 |
| Attagel 50 clay | 2.5 | 6 |
| Let Down | | |
| Latex | 153.0 | 367.1 |
| Colloid 643 | 1.5 | 3.6 |
| Texamol coalescent | 4.7 | 11.3 |
| Ammonia (28%) | 1.16 | 2.8 |
| Natrosol 250 MHR (2.5%) | 53.50 | 128.4 |
| Water | 54.46 | 130.8 |
| | 581.17 | 1394.9 |

In Table 5 are presented results for 5 days aging, and in Table 6 for 10 days aging at 60° C.

TABLE 5
LATEX PAINT CONTAINING 4,5-DICHLORO-2-OCTYL-3-ISOTHIAZOLONE PRESERVATIVE PLUS BISMUTH STABILIZER

| Preservative, ppm | Bismuth Stabilizer | ppm $Bi^{+3}$ | % AI Remaining |
|---|---|---|---|
| 800 | — | — | 0 |
| 100 | Sodium tartrate | 38 | 26 |
| 200 | Sodium tartrate | 75 | 11 |
| 400 | Sodium tartrate | 15 | 0 |
| 800 | Sodium tartrate | 38 | 0 |
| 100 | Octoate | 38 | 37 |
| 200 | Octoate | 75 | 11 |
| 400 | Octoate | 15 | 0 |
| 800 | Octoate | 38 | 0 |

Table 6 further illustrates that bismuth salts may be used to stabilize several isothiazolones in a paint formulation. It will be seen from Examples 5 and 6 that the ratio of bismuth compound to isothiazolone to achieve stabilization was significantly higher than for the metal working fluids of Examples 1-3. It is also noted that 2-octy-3-lisothiazolone showed no loss of AI under the test conditions of this experiment (10 days at 60° C.) when originally charged to the paint at 800 ppm, whether or not bismuth octoate was present.

TABLE 6
STABILITY OF VARIOUS ISOTHIAZOLONES PRESERVATIVES WITH BISMUTH OCTOATE IN A PAINT FORMULATION

| Isothiazolone, AI (ppm) | Stabilizer, ppm $Bi^{+3}$ | % AI Remaining |
|---|---|---|
| 5-chloro-2-methyl 15 | — | 0 |

TABLE 6-continued

STABILITY OF VARIOUS
ISOTHIAZOLONES PRESERVATIVES WITH
BISMUTH OCTOATE IN A PAINT FORMULATION

| Isothiazolone, Al (ppm) | Stabilizer, ppm $Bi^{+3}$ | % Al Remaining |
|---|---|---|
| " | " | 30 | 0 |
| " | " | 500 | 0 |
| " | " | 2000 | 23 |
| 4,5-di-Cl-2-octyl | 800 | — | 0 |
| " | " | 30 | 0 |
| " | " | 500 | 60 |
| " | " | 2000 | 100 |

While the invention has been described with reference to specific examples and applications, other modifications and uses for the invention will be apparent to those skilled in the art without departing from the spirit and scope of the invention defined in the appended claims.

What is claimed is:

1. A stabilized composition comprising:
   a) a compound of the formula

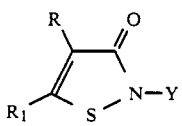

wherein Y is selected from the group consisting of alkyl or halogen- or hydroxy-substituted alkyl, unsubstituted or halo substituted alkenyl or alkynyl, cycloalkyl, ($C_7$) aralkyl or halogen- or alkoxy-substituted ($C_7$) aralkyl, ($C_6$) aryl or halogen- or alkoxyl-substituted ($C_6$)aryl, and hydrogen, and R and $R_1$ independantly selected from the group consisting of hydrogen, halo and ($C_1$-$C_4$)alkyl; and
   b) a stabilizing amount of a bismuth salt of an organic carboxylic acid, bismuth phosphate, or bismuth sulfate.

2. The composition of claim 1 which comprises from about 0.0001 to about 99.9999 parts of said compound and from about 0.0001 to 99.99 parts of said salt.

3. The composition of claim 1 which comprises from about 0.0001 to about 50 parts of said isothiazolone; from about 0.0001 to about 10 parts of said bismuth salt, and which further comprises from about 40 to about 99.9998 parts of solvent.

4. The composition of claim 3 which comprises from 1 to 25 parts of said isothiazolone, from 0.1 to 10 parts of said bismuth salt and from 65 to 98.9 parts of said solvent.

5. The composition of claim 1 wherein Y is selected from the group consisting of ($C_1$-$C_{18}$)alkyl and ($C_3$-$C_{12}$) cycloalkyl; R is selected from the group consisting of hydrogen, methyl and chloro; and $R_1$ is selected from the group consisting of hydrogen and chloro.

6. The composition of claim 5 wherein said isothiazolone is selected from the group consisting of 5-chloro-2-methyl-3-isothiazolone, 2methyl-3-isothiazolone, 4,5-dichloro-2-cyclohexyl-3-isothiazolone, 2-octyl-3-isothiazolone, or 4,5-dichloro-2-octyl-3-isothiazolone.

7. The composition of claim 6 wherein said isothiazolone is a mixture of from about 70 to about 85 parts of 5-chloro-2-methyl-3-isothiazolone, and about 15 to 30 parts of 2-methyl-3-isothiazolone.

8. The composition of claim 7 wherein said solvent is water.

9. The composition of claim 1 wherein said bismuth salt is of an acid selected from the group consisting of tartrate, mono(alkaline) tartrate, citrate, salicylate, octoate, oxalate, phosphate, acetate, and lactate.

10. A method for inhibiting the growth of bacteria, fungi, yeast or algae in a locus subject to contamination by bacteria, fungi, yeast or algae, which comprises incorporating onto or into said locus, in an amount which is effective to adversely affect the growth of bacteria, fungi, yeast, or algae, a composition according to claim 1.

11. The method of claim 10 wherein said locus is an aqueous medium.

12. The method of claim 10 wherein said locus is a metal working fluid formulation.

13. The method of claim 10 wherein said locus is a water-cooling system.

14. The method of claim 10 wherein said locus is a solid protective or decorative film.

15. The method of claim 10 wherein said locus is fabric, leather, paper, or wood.

16. The method of claim 10 wherein said locus is laundry wash water.

17. The method of claim 10 wherein said locus is a cosmetic formulation.

18. The method of claim 10 wherein said locus is a fuel system.

19. The method of claim 10 wherein said locus is plastic.

20. The method of claim 10 wherein said locus is an emulsion.

21. The method of stabilizing a composition comprising a 3-isothiazolone compound by addition of 0.0001 to 99.99 parts of a bismuth salt of an organic carboxylic acid, bismuth phosphate, or bismuth sulfate in the presence of an inert solvent.

* * * * *